US012796998B2

(12) United States Patent
Govari

(10) Patent No.: US 12,796,998 B2
(45) Date of Patent: Nov. 17, 2026

(54) IDENTIFYING FOCAL SOURCES OF ARRHYTHMIA WITH MULTI ELECTRODE CATHETER

(71) Applicant: BIOSENSE WEBSTER (ISRAEL) LTD., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 831 days.

(21) Appl. No.: 18/081,756

(22) Filed: Dec. 15, 2022

(65) Prior Publication Data

US 2024/0197234 A1 Jun. 20, 2024

(51) Int. Cl.

| | |
|---|---|
| ***A61B 5/367*** | (2021.01) |
| ***A61B 5/00*** | (2006.01) |
| ***A61B 5/287*** | (2021.01) |
| ***A61B 5/339*** | (2021.01) |
| ***A61B 5/361*** | (2021.01) |

(52) U.S. Cl.

CPC .............. *A61B 5/367* (2021.01); *A61B 5/287* (2021.01); *A61B 5/339* (2021.01); *A61B 5/361* (2021.01); *A61B 5/7221* (2013.01)

(58) Field of Classification Search

CPC ................................ A61B 5/361; A61B 5/367

USPC .......................................................... 600/508

See application file for complete search history.

(56) References Cited

U.S. PATENT DOCUMENTS

| | | | |
|---|---|---|---|
| 5,391,199 | A | 2/1995 | Ben-Haim |
| 5,443,489 | A | 8/1995 | Ben Haim |
| 5,558,091 | A | 9/1996 | Acker |
| 6,172,499 | B1 | 1/2001 | Ashe |
| 6,239,724 | B1 | 5/2001 | Doron |
| 6,332,089 | B1 | 12/2001 | Acker |
| 6,484,118 | B1 | 11/2002 | Govari |
| 6,618,612 | B1 | 9/2003 | Acker |
| 6,690,963 | B2 | 2/2004 | Ben Haim |
| 6,788,967 | B2 | 9/2004 | Ben Haim |
| 6,892,091 | B1 | 5/2005 | Ben Haim |
| 7,536,218 | B2 | 5/2009 | Govari |
| 7,756,576 | B2 | 7/2010 | Levin |

(Continued)

FOREIGN PATENT DOCUMENTS

EP 3354197 A1 * 8/2018 ............. A61B 5/361

OTHER PUBLICATIONS

European Search Report for corresponding EPA No. 23216505.0 dated May 17, 2024.

*Primary Examiner* — Nicole F Johnson

(57) ABSTRACT

A system for computing an electro-anatomical (EA) map of signals from tissue inside a chamber of a patient's includes a processor and a display. The processor receives electrophysiological (EP) signals from a plurality of electrodes on a distal end assembly of a catheter placed in the chamber, selects a contiguous sub-group of the plurality of electrodes and applies a consistency test to the EP signals acquired by the contiguous sub-group to determine if the EP signals from the sub-group of the electrodes display a common cycle length. When the consistency test is successful, the processor identifies a region in the chamber from which the EP signals have been acquired. The display renders an electro-anatomical (EA) map of the chamber and provides indicating on the rendered display of the region.

21 Claims, 3 Drawing Sheets

(56) References Cited

U.S. PATENT DOCUMENTS

| | | | | |
|---|---|---|---|---|
| 7,848,787 | B2 | 12/2010 | Osadchy | |
| 7,869,865 | B2 | 1/2011 | Govari | |
| 8,456,182 | B2 | 6/2013 | Bar-Tal | |
| 10,582,894 | B2 | 3/2020 | Ben Zrihem | |
| 2015/0227702 | A1 * | 8/2015 | Krishna ................. | A61B 5/374<br>705/2 |
| 2015/0342488 | A1 * | 12/2015 | Laughner ............... | A61B 5/361<br>600/509 |
| 2019/0336023 | A1 | 11/2019 | Lou et al. | |

* cited by examiner

IDENTIFYING FOCAL SOURCES OF ARRHYTHMIA WITH MULTI ELECTRODE CATHETER

FIELD OF THE DISCLOSURE

This disclosure relates generally to analysis of electrophysiological (EP) signals, and specifically to a method for identifying tissue sources of focal arrhythmia.

BACKGROUND OF THE DISCLOSURE

Identifying arrhythmogenic tissue regions in the heart using a mapping catheter was previously proposed in the patent literature. For example, U.S. Pat. No. 10,582,894 describes a method of atrial rotational activity pattern (RAP) source detection, where RAP is one of the proposed mechanisms for atrial fibrillation maintenance. The method includes detecting, via a plurality of sensors, electro-cardiogram (ECG) signals over time, each ECG signal detected via one of the plurality of sensors and indicating electrical activity of a heart. The method also includes determining, for each of the plurality of ECG signals, one or more local activation times (LATs) each indicating a time of activation of a corresponding ECG signal. The method further includes detecting whether one or more RAP source areas of activation in the heart is indicated based on the detected ECG signals and the one or more local LATs. Mapping information of the detected RAP source areas of activation in the heart is also generated for providing one or more maps.

The present disclosure will be more fully understood from the following detailed description of the examples thereof, taken together with the drawings, in which:

DETAILED DESCRIPTION OF EXAMPLES

Overview

Figure 1:
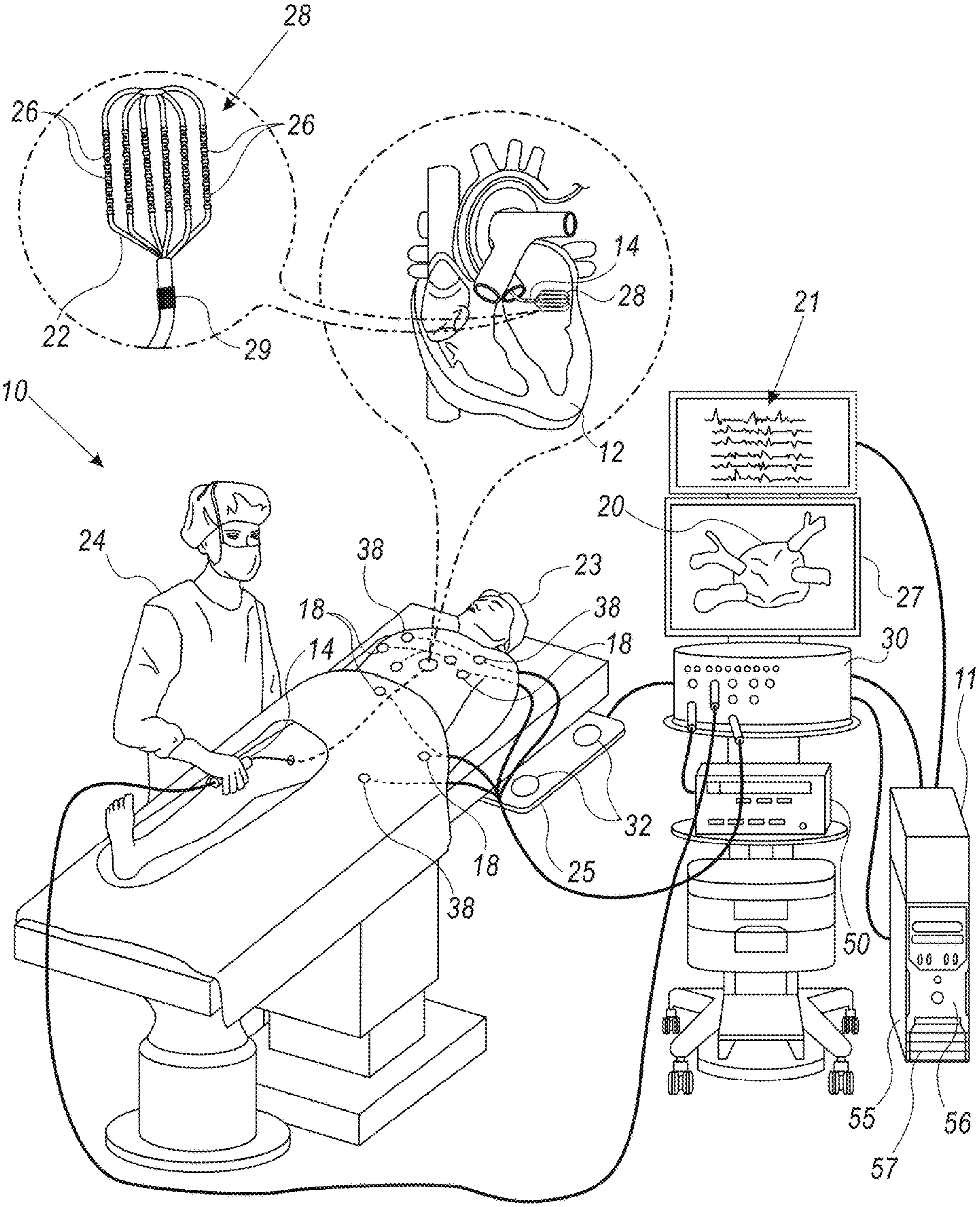
FIG. 1 is a schematic, pictorial illustration of a catheter-based electrophysiology (EP) mapping and ablation system, in accordance with an example of the present disclosure.

In order to characterize an arrhythmia of a patient, such as atrial fibrillation (AF), a catheter-based electrophysiology (EP) mapping system may be used to generate an EP map of least part of the heart of the patient, such as of an atrium. Typically, such EP map comprises local EP tissue characteristics (e.g., local activation time (LAT), or local cycle time (CL) between activations) overlaid on an anatomical map of the cardiac chamber. The EP map is meant to show arrhythmogenic sources and pathways in the atrium wall tissue, so as to guide a physician to the best locations at which to ablate tissue in order to suppress the arrhythmia.

Typically, in treatment of AF, the physician will look in the EP map for isolated areas with one or more tissue locations of focal arrhythmia (also called hereinafter "focal sources"), and consider such areas as candidates for ablation. Such "spots" of arrhythmogenic focal sources with a characteristic time stamp are targets as they are sources of arrhythmogenic activity leading to the AF.

In a typical catheter-based EP mapping procedure, a distal end of a catheter, which comprises multiple sensing electrodes, is inserted into the cardiac chamber to sense EP signals, such as unipolar and/or bipolar electrograms (EGM). As a physician operating the system moves the distal end inside the cardiac chamber, the EP-mapping system acquires EP signals at numerous locations on the inner surface of the cardiac chamber. At the same time the system records the respective positions of the distal end.

A multi-electrode catheter, such as a multi-arm catheter, has about 100 electrodes that can capture at a given instance a hundred intracardiac ECG signals even over a limited area. Therefore, such EP mapping procedure may generate a vast amount of information to analyze, up to few tens of thousands of data points (each comprising an EP signal and a position). Cardiac wave propagation analysis based on output from all the electrodes may yield a chaotic pattern, because this is how AF is electrophysiologically manifested when observed over a large area.

The interpretation of an EP map is therefore not always straightforward. For example, in AF, propagation of the cardiac action potential appears chaotic in time, and fractionated actional potentials (e.g., irregular patterns such as bursts of highly rapid deflections of the EGM) may be observed. One reason for such disordered signals is due to a plurality of arrhythmogenic focal sources concurrently initiating activation. Another reason may be due to scar tissue. Cycle length in a region of scar tissue may be longer than the cycle length associated with sinus rhythm. In the process, the focal sources themselves are not readily apparent in the chaotic propagation. It is therefore difficult to make any sense (e.g., identify the required time stamp) out of this seemingly random pattern. Without identifying the focal sources, a physician will have difficulty in understanding where to ablate.

Examples of the present disclosure that are described herein provide a technique in which a processor runs a program to search for organized patterns within the seemingly-chaotic propagation patterns of the EP map. To this end, the processor separately examines outputs from sub-groups of contiguous electrodes of a multi-electrode EP mapping catheter. When identifying an organized pattern, the processor uses the organized pattern to direct the physician to one or more focal sources. Optionally, the physician can choose to ablate these.

In the present context, the term "organized pattern" refers to a set of EP measurements (e.g., cycle lengths, activation frequencies or local activation times) that are measured by a contiguous sub-group of electrodes and are self-consistent with one another according to a defined consistency test, such as sharing a same CL within tight tolerance (e.g., all presenting a sinus rhythm).

In the disclosed technique, the processor selects one or more sub-groups of electrodes, from among the numerous electrodes of the mapping catheter. In one example of the disclosed method, the processor examines local cycle lengths (or activation frequencies, if implementation is in the frequency domain using unit of HR=60,000/CL [BPM] for CL given in milliseconds) to find areas that are being activated from a same focal source. Electrograms possessing peaks at long cycle lengths that are constant in time and space can be considered to be activated from such same source. If frequency domain analysis is used by, for example, applying FFT to electrograms, then the criterion is specified in terms of frequency. This way, electrograms possessing peaks low at frequencies (lower than characteristic frequency of sinus rhythm) that are constant in time and space can be considered to be activated from such source. A same frequency domain chart of representative power spectrum (e.g., sum or average of FFT power spectrum over a subgroup of electrodes) can be presented in Hz units, where center heart rate in Hz is given using 1000/t [1/sec] for t given in milliseconds.

To this end, the processor may apply a consistency test to the sub-group of CL values, such as by defining a criterion for a sub-group of CL values to be considered as constant in time and space. In one example, the criterion is based on a histogram of the sub-group CL values about a representative CL value (median or maximal CL value) being narrow enough, e.g., below a defined width threshold. Another criterion may be based on a histogram of the sub-group LAT values being narrow enough, e.g., below a defined width threshold. In this disclosure, a representative CL in time domain is equivalent to a representative heart rate in the frequency domain, using the aforementioned time-frequency conversion.

For each local organized pattern detected, the focal source of such a pattern may then be identified by a processor by the aforementioned comparison to sinus rhythm and acceptability testing. The processor may compare the local cycle length (or local frequency of activation) to that of a normal, global, sinus rhythm cycle length (or heart rate frequency) of the heart. If a sub-group of contiguous electrodes exhibit a same frequency (or cycle length) that is other than the sinus rhythm, the processor may provide indication of this region on a map of the chamber. When the local cycle length found is other than the sinus CL, the processor indicates this region in association with its cycle length to the user on an EP map.

In some examples, to best identify such areas, the processor attempts different divisions into sub-groups (including different sized and shaped sub-groups) to search for regions with a same cycle length. If the processor cannot find such organized pattern, the processor divides at least portion of the numerous electrodes into differently shaped sub-group, and/or divides the sub-groups into smaller sub-groups and tries again. The process may be iterative, to find a sub-group of electrodes that best meets the above set criteria. Based on this division, the processor may build a map of the chamber and indicate the areas that have the same cycle length and thereby may be activated by the same focal source.

System Description

FIG. 1 is a schematic, pictorial illustration of a catheter-based electrophysiology (EP) mapping and ablation system 10, in accordance with an example of the present disclosure.

System 10 includes multiple catheters, which are percutaneously inserted by physician 24 through the patient's vascular system into a chamber or vascular structure of a heart 12. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example catheter 14 that is configured for sensing IEGM is illustrated herein. Physician brings a distal tip 28 (also called hereinafter "distal end assembly 28") of catheter 14 into contact with the heart wall for sensing a target site in heart 12. For ablation, physician 24 would similarly bring a distal end of an ablation catheter to a target site for ablating.

Catheter 14 is an exemplary catheter that includes one and preferably multiple electrodes 26 optionally distributed over a plurality of splines 22 at distal tip 28 and configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of magnetic coils 32 configured to generate magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described in U.S. Pat. Nos. 5,5391, 199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

A recorder 11 displays electrograms 21 captured with body surface ECG electrodes and 18 intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory 57, processor 56 unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Identifying Focal Sources of Arrhythmia with Multi Electrode Catheter

Figure 2:
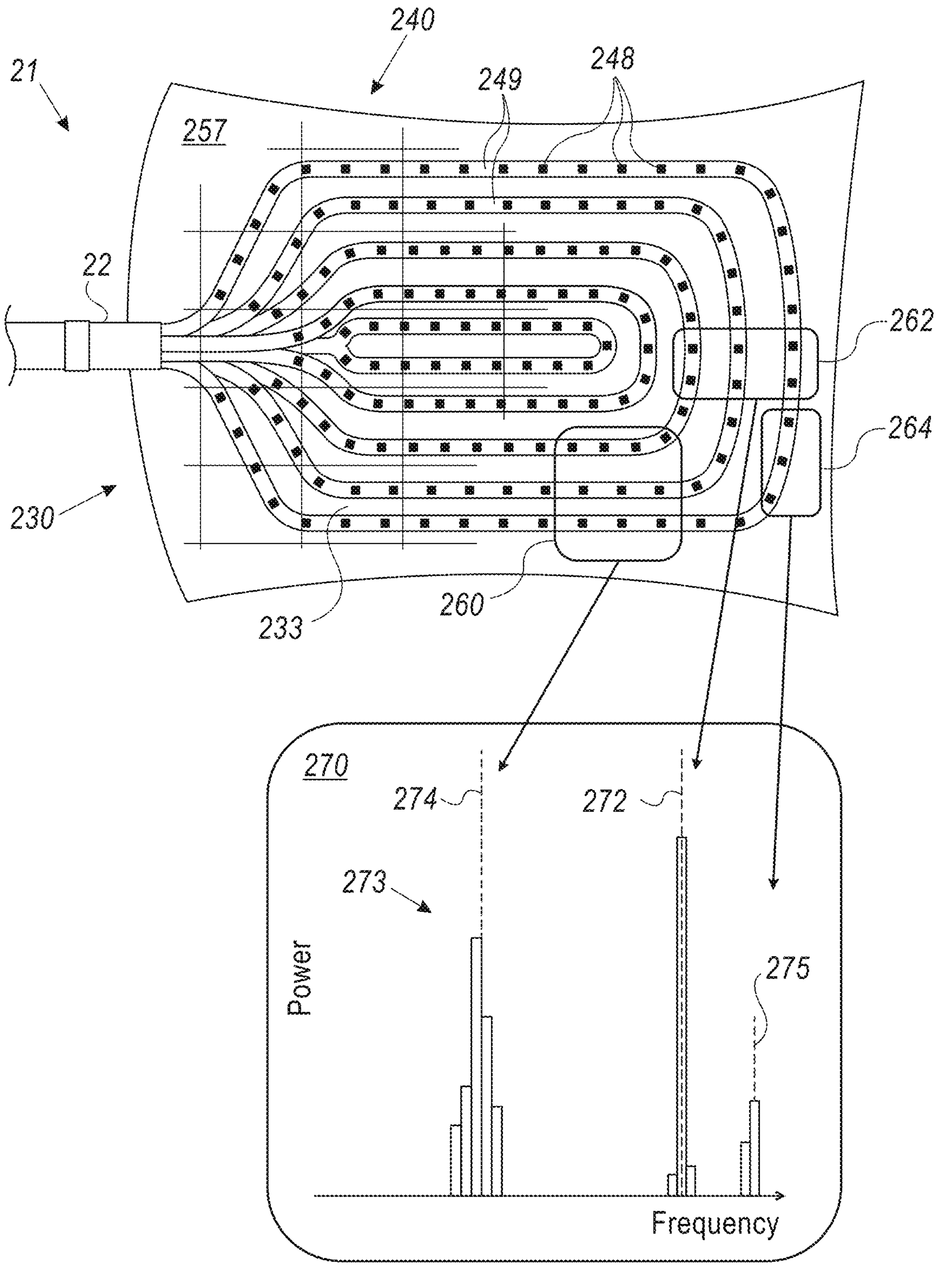
FIG. 2 is a schematic, pictorial illustration of a catheter acquiring EP data points inside a cardiac chamber and a graph of an arrhythmia-indicative representative power spectrum computed from Fast Fourier Transform (FFT) of EP data points acquired therein, in accordance with an example of the present disclosure.

FIG. 2 is a schematic, pictorial illustration of a catheter acquiring EP data points inside a cardiac chamber and a graph of an arrhythmia-indicative representative power spectrum computed from FFT of EP data points acquired therein, in accordance with an example of the present disclosure. The catheter in the shown example is catheter 14 with flat distal end assembly 240, which is same or similar to distal end assembly 28 of FIG. 1. Distal end assembly 240 comprises multiple splines 249 that carry multiple sensing electrodes 248.

Flat distal end assembly 240 is seen being attached to a portion 257 of a wall tissue of a left atrium, with electrodes 248 acquiring EP signals, such as bipolar electrograms.

As described above, during analysis, processor 56 runs a program to examine output from contiguous sub-groups of electrodes 248, such as within areas 260 and 262 of flat catheter's distal end assembly 240.

The processor extracts, using FFT, power spectrum of electrograms for each electrode in these areas, the representative power spectrum seen in graph 270. The schematically shown spectra are generated by accumulating spectrums of individual EGMs acquired each from individual electrodes of a same area.

Analysis of EP signals from area 262 reveals a well-defined peak centered about a global sinus rhythm value 272 of the accumulated spectrum. This means normal, healthy, tissue region was mapped under area 262. A well-defined peak 273 of the accumulated spectrum, on the other hand, reveals a consistent frequency range that has a representative frequency value 274 (e.g., mean activation frequency value). Such a peak (narrowly distributed, but around an exceedingly small representative frequency value) is typically indicative of an arrhythmogenic tissue region that was mapped under area 262 at the time the EP signals were acquired. Representative frequency value 274 is distinctively lower than the normal heart rate value.

Analysis of EGMs from acquired from another region of cardiac tissue, under area 264 of contiguous electrodes, reveals a high frequency well-defined peak 275.

Figure 4:
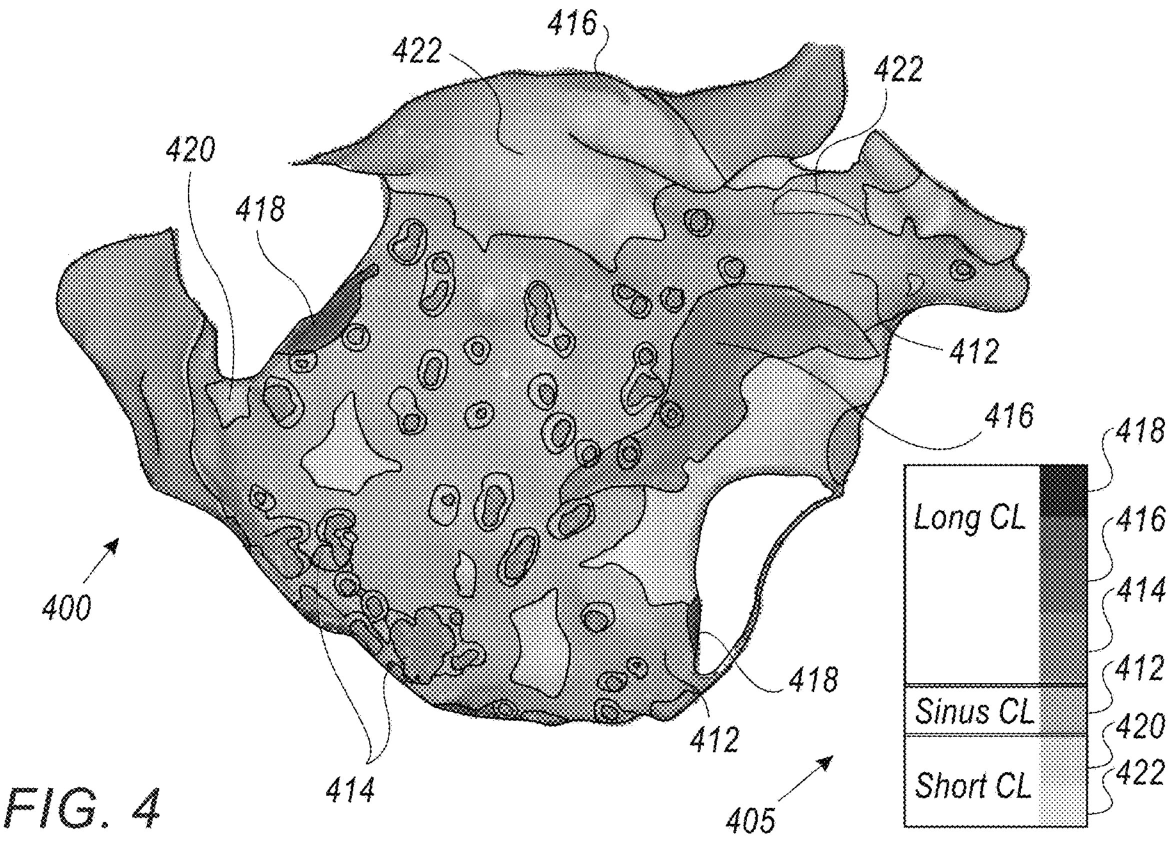
FIG. 4 is a schematic, pictorial volume rendering of an EP map of a left atrium indicating tissue regions exhibiting each a common characteristic cycle length (CLs) different than a characteristic sinus cycle length, in accordance with an example of the present disclosure.

As catheter 14 is equipped with position sensor 29, seen in FIG. 1 the low frequency 274 (long CL) arrhythmogenic tissue region that was mapped under area 260 can be indicated by processor 56 on an EP map 400, as seen in FIG. 4. Map 400 would also show regions of normal sinus rhythm and any spots or regions with the high activation frequencies 275. Typically, EP map is color coded to show the entire range of activation frequencies, and typically the EP map is provided in terms of CL as a spatiotemporal activation map, as defined above.

In another example, processor 56 runs an algorithm that divides the area of catheter's distal end assembly 240 by grid 230 areas 233, to examine output from sub-groups of electrodes 248 inside areas 233. The FFT analysis is performed as above, in search of at least one area 233 with a representative power spectrum that shows a narrowly distributed peak, that is spread around an exceedingly small representative frequency value.

If none is found, the processor can change grid 230 parameters (e.g., periodicities), to, for examples, examine representative power spectra from smaller areas 233.

FIG. 2 is brought by way of example and is simplified to convey the concept in clarity. In particular, shapes of contiguous areas such as 260, 262 and 264 are simplified in FIG. 2, but can be complex ones, such as including lobes.

Figure 3:
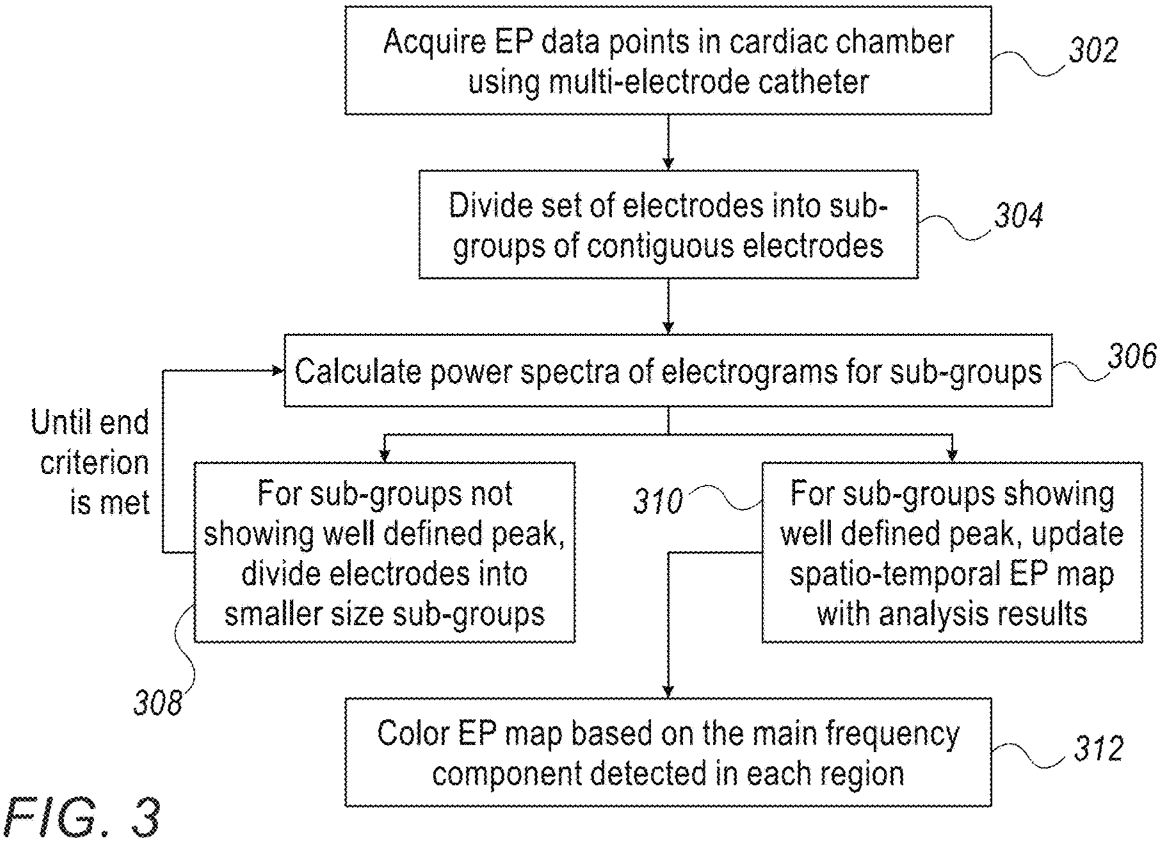
FIG. 3 is a flow chart that schematically illustrates a method to identify suspect arrhythmogenic sources in wall tissue of a cardiac chamber, in accordance with an example of the present disclosure.

FIG. 3 is a flow chart that schematically illustrates a method to identify suspect arrhythmogenic sources in wall tissue of a cardiac chamber, in accordance with an example of the present disclosure. The algorithm, according to the presented example, carries out a process that begins with acquiring EP data points inside a cardiac chamber such as a left atrium using system 10 of FIG. 1 and catheter 14 described further in of FIG. 2, at EP data acquisition step 302. The catheter may be a multi electrode catheter, such as a basket catheter or a flat shaped catheter, e.g., such as the flat shaped catheter shown in FIG. 1.

In catheter electrode array virtual division step, the processor divides the electrode array (e.g., the set of electrodes) into sub-groups of contiguous electrodes, as demonstrated in FIG. 2A.

In EP data analysis step 306, processor 56 runs a program to examine output from the sub-groups of contiguous electrodes 248 by calculating a representative power spectrum for each sub-group, such as demonstrated in FIG. 2B.

Next, processor 56 performs FFT on the output to identify whether one or more of the sub-groups of contiguous electrodes 248 that exhibit a common frequency component, e.g., substantive peak in the power spectrum. In one example, processor 56 checks if the accumulated sensed voltage in each area of contiguous electrodes shows a well-defined peak, such as any of the peaks shown in FIG. 2B. This stage is represented by two steps: in analysis of arrhythmogenic activity step 308 the processor considers sub-groups that do not show a well-defined peak, whereas in analysis of arrhythmogenic activity step 310 the processor considers sub-groups that show a well-defined peak.

Based on Step 308, the processor iterates the analysis by reducing the size of the sub-group in an attempt to receive a well-defined peak. The iterations may stop at a minimal size of a subgroup, or by another conditions, such as reaching a maximal number of iterations. An iteration may also include changing a shape of an area, like to into different shapes, some of which are seen in FIG. 2A.

For peaks in representative power spectra that passed the test, e.g., showing in analysis step 310 a well-defined peak, processor 56 compares the representative frequency detected to a frequency associated with sinus rhythm. The frequency associated with sinus rhythm may be determined from a region that is known to be healthy and the value may be stored in memory.

Finally, the processor graphically indicates (e.g., colors) any region having a common frequency on an anatomical map of the chamber in step 312. The indication is relative to the frequency associated with sinus rhythm. This way the physician can see what regions are being activated by a focal source, what regions are scar tissue regions and what regions are activated by sinus rhythm. Based on the map, the physician can readily depict areas that have a cycle length that is greater than sinus and regions that are less than sinus. Also, the degree at which the cycle is different than sinus can be depicted. This would be evident on the EP map of FIG. 4.

The flow chart shown in FIG. 3 is chosen purely for the sake of conceptual clarity. The present example may also comprise additional steps of the algorithm, such as pre-selecting input EGMs based on indications of the degree of physical contact of the electrodes with diagnosed tissue from a contact force sensor. This and other possible steps are omitted from the disclosure herein purposely in order to provide a more simplified flow chart.

FIG. 4 is a schematic, pictorial volume rendering of an EP map 400 of a left atrium indicating tissue regions exhibiting each a common characteristic cycle length (CLs) different than a characteristic sinus cycle length, in accordance with an example of the present disclosure.

The map graphically indicates (e.g., colors) regions with the same cycle length (up to a tolerance) with the same color. In one example, sinus rhythm is represented by a defined color 412 and the other regions are different colors depending on their characteristic cycle length as compared to sinus cycle length. A color scale 405 assist user to read the map. In another example, the color scale can be a rainbow scale so that a physician can easily identify where each color is in the range.

EP map 400 can be a CL map or equivalently, a frequency map. Regions 414, 416, and 418 of respective long CL values Normal tissue regions 412 will be associated with the characteristic sinus CL 412. Regions 420 and 422 are regions with short cycle lengths.

Based on EP map 400, a physician 30 can plan and perform a careful, selective ablation to eliminate AF with minimal hazard to the patient.

EXAMPLES

Example 1

A system (10) includes a processor (56) and a display (27). The processor is configured to receive electro-physiological (EP) signals (21) from a plurality of electrodes (26) on a distal end assembly (28) of a catheter in the chamber, (b) apply a consistency test to the EP signals acquired by the contiguous sub-group to determine if the EP signals from the sub-group of the electrodes display a common cycle length (c) when the consistency test is successful, identify a region in the chamber from which the EP signals have been acquired by the contiguous sub-group. The display (27) is configured to render an electro-anatomical (EA) map (20) of the chamber and to indicate the region on the rendered EA map (20).

Example 2

The system according to example 1, wherein the processor (56) is configured to calculate power spectra (270) for the EP signals acquired by the electrodes in the sub-group, and to apply the consistency test to the power spectra.

Example 3

The system according to any of examples 1 and 2, wherein, when the consistency test is successful, the processor (56) is configured to compare a representative frequency value (274, 275) of the sub-group to a sinus frequency value (272) of the heart, and provide indication (420, 422) if the representative frequency value is smaller than the sinus frequency by a minimum amount.

Example 4

The system according to any of examples 1 and 2, wherein, when the consistency test is unsuccessful, the processor (56) is further configured to select a smaller contiguous sub-group of the electrodes of the catheter and apply a consistency test to the EP signals acquired by the electrodes (26) in the smaller sub-group.

Example 5

The system according to any of examples 1 and 2, wherein the processor (56) is configured to apply the consistency test by estimating a width of a peak of a representative power spectrum peak (274, 275) for the sub-group.

Example 6

The system according to any of examples 1 through 5, wherein the processor (56) is configured to calculate local Cycle Length (CL) values for the EP signals acquired by the electrodes in the sub-group, and to apply the consistency test to the local CL values.

Example 7

The system according to any of examples 1 through 6, wherein, when the consistency test is successful, the (56) processor is configured to compare a representative CL value of the sub-group to a sinus CL value of the heart, and provide indication (414, 416, 418) if the representative CL value is larger than the sinus CL value by a minimum amount.

Example 8

The system according to any of examples 1 through 6, wherein the processor (56) is further configured to graphically encode (405) on an EP map (400), regions (414, 416, 418, 420, 422) with representative CL values that larger or smaller compared to a representative sinus CL value.

Example 9

The system according to any of examples 1 through 6, wherein the processor (56) is configured to apply the consistency test by estimating a width of a histogram of the CL values of the sub-group.

Example 10

The system according to any of examples 1 through 10, wherein EP signals are one of unipolar and bipolar electrograms (21).

Example 11

A method for rendering and electro-anatomical (EA) map of signals from tissue inside a chamber of a patient's heart, the method includes:

acquiring multiple respective electrophysiological (EP) signals (21) from tissue inside a heart (12) of patient (23) using a catheter comprising a distal end assembly (28) having multiple electrodes (26);

selecting a contiguous sub-group (260, 262, 264) of the electrodes (26) of the catheter;

applying a consistency test to the EP signals (21) acquired by the electrodes (26) in the sub-group to determined that the EP signals from the sub-group of the electrodes display a common cycle length; and when the consistency test is successful, identify a region in the chamber from which the EP signals have been acquired by the contiguous sub-group and indicating the region on an EA map (20) of the heart that is rendered on a display (27).

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

The invention claimed is:

1. A system configured for rendering an electro-anatomical (EA) map of a cardiac chamber of a patient's heart, the system comprising:

a catheter configured to be inserted into the cardiac chamber, the catheter having a distal end carrying a plurality of electrodes, each of the plurality of electrodes being configured to collect electro-physiological (EP) signals from cardiac tissue;

a controller configured to concurrently sample the EP signals from the plurality of electrodes;

a processor, coupled with the controller, and configured to:

receive the EP signals determine a sinus cycle length of the patient's heart;

select a contiguous sub-group of the plurality of electrodes, the sub-group including physically contiguous electrodes;

apply a consistency test to the EP signals acquired by the contiguous sub-group, to determine whether EP signals from a contiguous subgroup of the electrodes exhibit a common cycle length;

when the consistency test is unsuccessful, dynamically select a different contiguous sub-group having at least one of a reduced size and a different shape, and automatically re-apply the consistency test to EP signals acquired by the different contiguous sub-group, the processor iteratively repeating the adjusting and re-applying until the consistency test is successful or a stopping condition is met;

when the consistency test is successful, identify a region in the chamber from which the EP signals have been acquired by the contiguous sub-group; and generate an EA map of the chamber as a cycle-length map by graphically encoding the region of the EA map according to the common cycle-length relative to the sinus cycle-length; and a display configured to display the EA map including the graphically encoded region, thereby allowing a user of the system to consider the region of the chamber as possible focal sources of arrhythmia.

2. The system according to claim 1, wherein the processor is configured to calculate power spectra for the EP signals acquired by the electrodes in the sub-group, and to apply the consistency test to the power spectra.

3. The system according to claim 2, wherein, when the consistency test is successful, the processor is configured to compare a representative frequency value of the sub-group to a sinus frequency value of the heart and provide indication if the representative frequency value is smaller than the sinus frequency by a minimum amount.

4. The system according to claim 2, wherein, when the consistency test is unsuccessful, the processor is further configured to select a smaller contiguous sub-group of the electrodes of the catheter and apply a consistency test to the EP signals acquired by the electrodes in the smaller sub-group.

5. The system according to claim 2, wherein the processor is configured to apply the consistency test by estimating a width of a peak of a representative power spectrum peak for the sub-group.

6. The system according to claim 1, wherein the processor is configured to calculate local Cycle Length (CL) values for the EP signals acquired by the electrodes in the sub-group, and to apply the consistency test to the local CL values.

7. The system according to claim 6, wherein, when the consistency test is successful, the processor is configured to compare a representative CL value of the sub-group to a sinus CL value of the heart and provide indication if the representative CL value is larger than the sinus CL value by a minimum amount.

8. The system according to claim 6, wherein the processor is further configured to graphically encode on an EP map, regions with representative CL values that larger or smaller compared to a representative sinus CL value.

9. The system according to claim 6, wherein the processor is configured to apply the consistency test by estimating a width of a histogram of the CL values of the sub-group.

10. The system according to claim 1, wherein EP signals are one of unipolar and bipolar electrograms.

11. The system of claim 2, wherein calculating the power spectra for each electrode comprises applying a Fast Fourier Transform (FFT) to the EP signals acquired by that electrode and identifying a dominant spectral peak from the resulting power spectrum.

12. A method for rendering an electro-anatomical (EA) map of a cardiac chamber of a patient's heart, the method comprising:

providing a catheter configured to be inserted into the cardiac chamber, the catheter having a distal end carrying a plurality of electrodes, each of the plurality of electrodes being configured to collect electro-physiological (EP) signals from cardiac tissue;

concurrently sampling the EP signals from the plurality of electrodes;

determining a sinus cycle length of the patient's heart;

selecting a contiguous sub-group of the electrodes of the catheter, the sub-group including physically contiguous electrodes;

applying a consistency test to the EP signals acquired by the contiguous sub-group, to determine whether EP signals from a contiguous subgroup of the electrodes exhibit a common cycle length;

when the consistency test is unsuccessful, dynamically selecting a different contiguous sub-group having at least one of a reduced size and a different shape, and automatically re-applying the consistency test to EP signals acquired by the different contiguous sub-group, iteratively repeating the adjusting and re-applying until the consistency test is successful or a stopping condition is met;

when the consistency test is successful, identifying a region in the chamber from which the EP signals have been acquired by the contiguous sub-group;

generating an EA map of the chamber as a cycle-length map by graphically encoding the region of the EA map according to the common cycle-length relative to the sinus cycle-length; and displaying the EA map including the graphically encoded region, thereby allowing a user of the system to consider the region of the chamber as possible focal sources of arrhythmia.

13. The method according to claim 12, and comprising calculating power spectra for the EP signals acquired by the electrodes in the sub-group, and to apply the consistency test to the power spectra.

14. The method according to claim 13, and comprising, when the consistency test is successful, comparing a representative frequency value of the sub-group to a sinus frequency value of the heart, and provide indication if the representative frequency value is smaller than the sinus frequency by a minimum amount.

15. The method according to claim 13, and comprising, when the consistency test is unsuccessful, selecting a smaller contiguous sub-group of the electrodes of the catheter and applying a consistency test to the EP signals acquired by the electrodes in the smaller sub-group.

16. The method according to claim 13, wherein applying the consistency test comprises estimating a width of a peak of a representative power spectrum peak for the sub-group.

17. The method according to claim 12, and comprising calculating local Cycle Length (CL) values for the EP signals acquired by the electrodes in the sub-group, and to apply the consistency test to the local CL values.

18. The method according to claim 17, and comprising, when the consistency test is successful, comparing a representative CL value of the sub-group to a sinus CL value of the heart, and providing indication if the representative CL value is larger than the sinus CL value by a minimum amount.

19. The method according to claim 17, and comprising graphically encoding on an EA map, regions with representative CL values that larger or smaller compared to a representative sinus CL value.

20. The method according to claim 17, wherein applying the consistency test comprises estimating a width of a histogram of the CL values of the sub-group.

21. The method according to claim 12, wherein EP signals are one of unipolar and bipolar electrograms.

* * * * *